United States Patent [19]

Yoon

[11] Patent Number: 5,676,681
[45] Date of Patent: Oct. 14, 1997

[54] SAFETY TROCAR PENETRATING INSTRUMENT WITH SAFETY SHIELD HAVING RESILIENT LEGS

[76] Inventor: InBae Yoon, 2101 Highland Ridge Dr., Phoenix, Md. 21131

[21] Appl. No.: 759,923

[22] Filed: Dec. 4, 1996

Related U.S. Application Data

[62] Division of Ser. No. 313,655, Sep. 26, 1994, Pat. No. 5,591,190, which is a continuation of Ser. No. 817,113, Jan. 6, 1992, Pat. No. 5,350,393.

[51] Int. Cl.$^6$ ................................................ A61B 17/34
[52] U.S. Cl. ........................ 606/185; 604/164; 604/264
[58] Field of Search ........................... 606/185; 604/164, 604/264, 272

[56] References Cited

U.S. PATENT DOCUMENTS

| | | |
|---|---|---|
| 1,248,492 | 12/1917 | Hill . |
| 4,023,559 | 5/1977 | Gaskell . |
| 4,535,773 | 8/1985 | Yoon . |
| 4,601,710 | 7/1986 | Moll . |
| 4,654,030 | 3/1987 | Moll et al. . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,104,382 | 4/1992 | Brinkerhoff et al. . |
| 5,112,321 | 5/1992 | Hiltebrandt . |

*Primary Examiner*—Michael H. Thaler

[57] ABSTRACT

A safety trocar penetrating instrument particularly useful in least invasive surgery includes a portal sleeve, a trocar disposed in the portal sleeve and having a sharp, solid, angled tissue penetrating distal end and a safety shield disposed in the portal sleeve and receiving the trocar, the safety shield being movable relative to the trocar between an extended position wherein a distal end of the safety shield protects the sharp tip and a retracted position exposing the sharp tip. The configuration of the distal ends of the trocar and the safety shield in the retracted position present a substantially continuous, angled surface for penetrating tissue. A hub receiving proximal ends of the trocar and safety shield includes a locking mechanism allowing the safety shield to be automatically or optionally locked in the extended position and permitting selective, releasable or automatic locking of the safety shield in the retracted position.

3 Claims, 3 Drawing Sheets

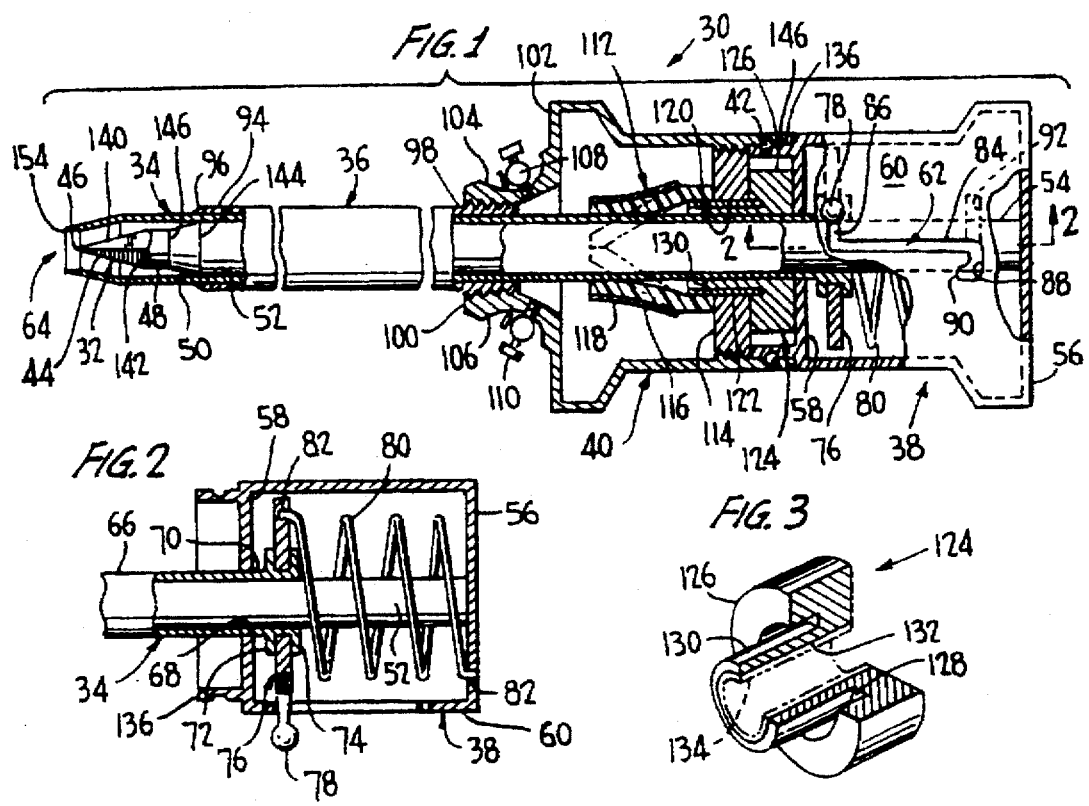
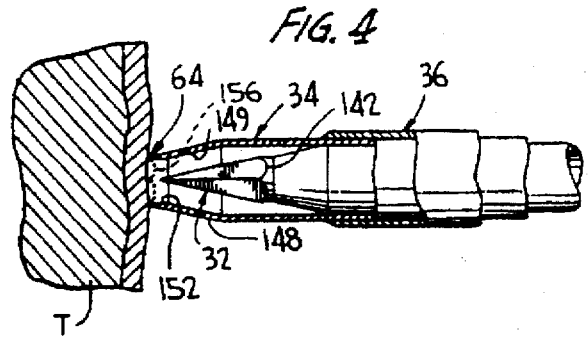
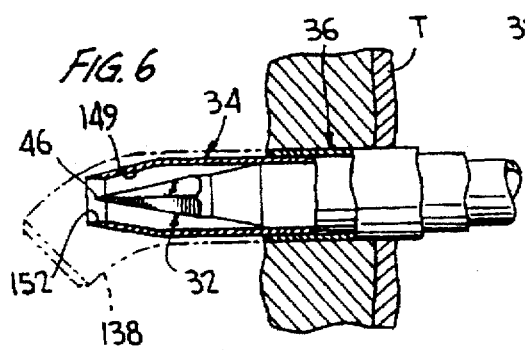
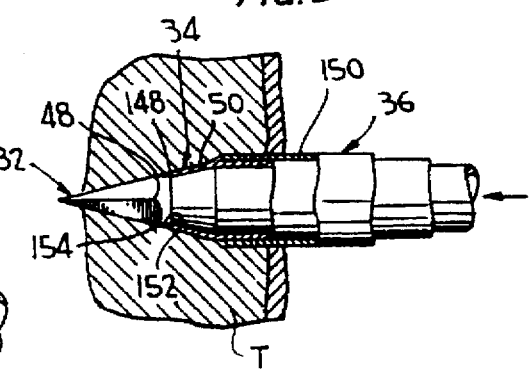

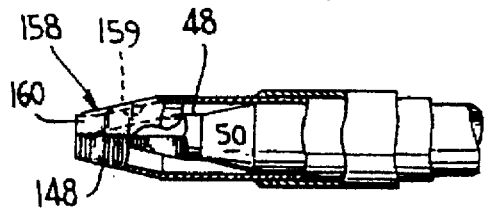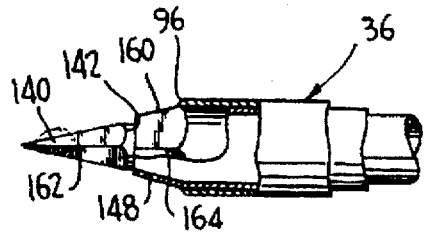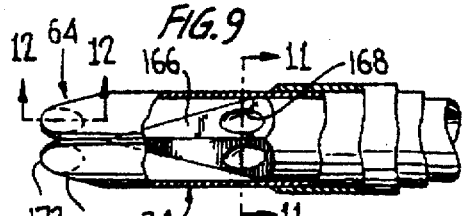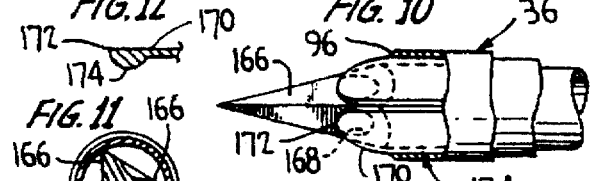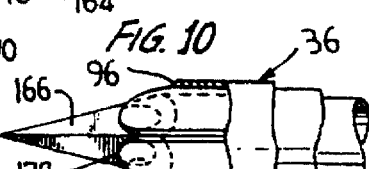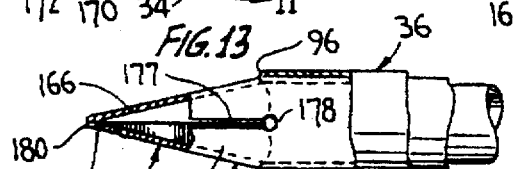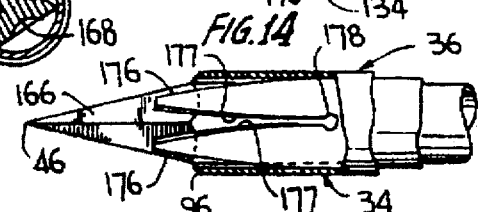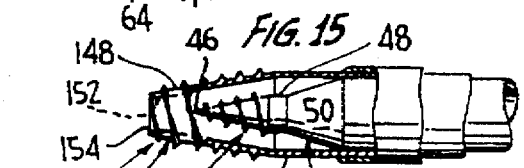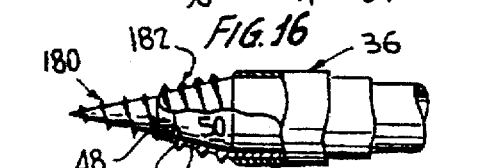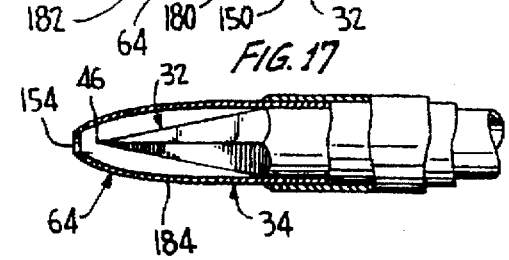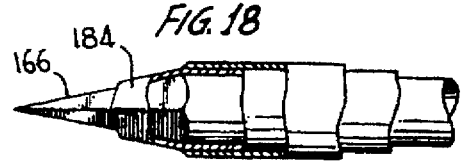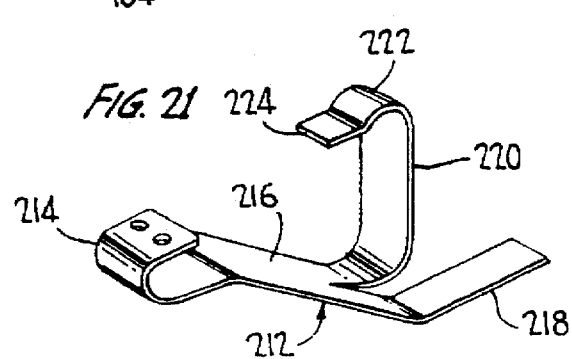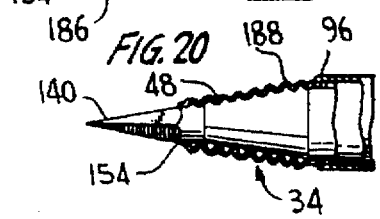

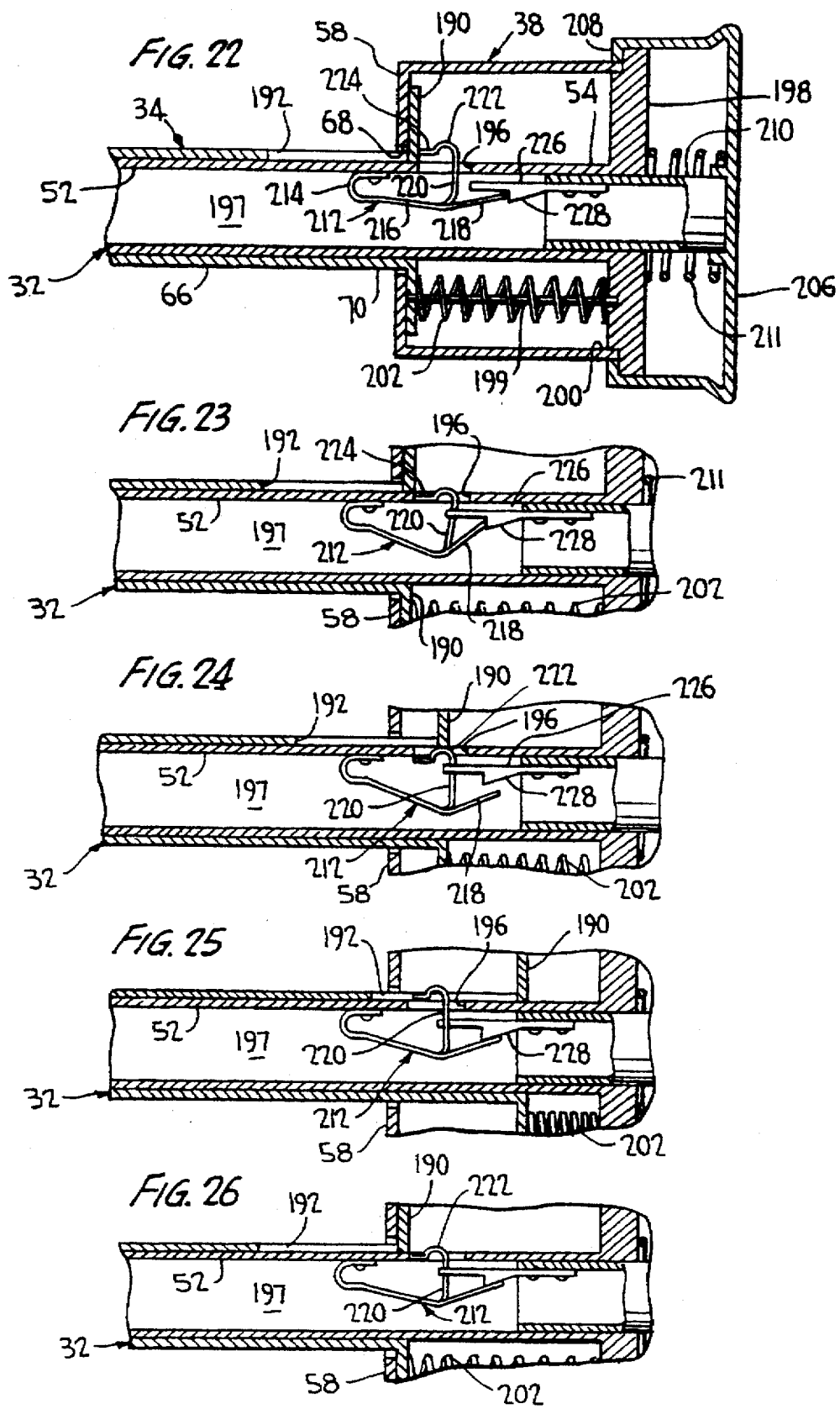

SAFETY TROCAR PENETRATING INSTRUMENT WITH SAFETY SHIELD HAVING RESILIENT LEGS

This application is a division of patent application Ser. No. 08/313,655, filed Sep. 26, 1994 now U.S. Pat. No. 5,591,190 which was a continuation of Ser. No. 07/817,113, filed Jan. 6, 1992, now U.S. Pat. No. 5,350,393.

BACKGROUND OF THE INVENTION

1. Field Invention

The present invention pertains to surgical penetrating instruments for accessing cavities within the body and, more particularly, to such penetrating instruments formed of trocars having solid, tissue penetrating, sharp tips and safety shields surrounding the trocars for preventing tissue from contacting the sharp tips after entry into body cavities.

2. Discussion of the Prior Art

Trocars are commonly used for accessing cavities within the body and establishing an endoscopic portal for various procedures to be performed by least invasive surgery. Portal sleeves or cannulas are normally disposed around the trocars to be positioned upon penetration into the cavity by the trocar. Trocars include a sharp tissue penetrating pyramidal distal end or tip to pierce or penetrate tissue forming the cavity wall, and the force required to penetrate the cavity wall is dependent upon the type and thickness of the tissue of the wall. Once the wall is penetrated, it is desirable to prevent the sharp tip of the trocar from inadvertently contacting tissue in or forming the cavity, and a particular problem exists where substantial force is required to penetrate the cavity wall in that, once penetration is achieved, the lack of tissue resistance can result in the sharp trocar tip traveling too far into the cavity and injuring adjacent tissue. Safety trocars having a spring-biased protective shield disposed between an outer portal sleeve and an inner trocar are marketed by Ethicon, Inc. as the Endopath and by United States Surgical Corporation as the Surgiport, and U.S. Pat. No. 4,535,773 to Yoon, U.S. Pat. No. 4,601,710 to Moll and U.S. Pat. No. 4,654,030 to Moll et al are exemplary of such safety trocars.

A disadvantage of prior art safety trocars is that the safety shields cannot be optionally locked in an extended position protecting the sharp trocar tips for safety in handling and use. A further disadvantage of prior art safety trocars is that the safety shields cannot be selectively retracted to expose the sharp trocar tips without a force being applied to the safety shields with tissue contact. Accordingly, the sharp trocar tips in prior art safety trocars cannot be effectively used in further penetration or treatment of tissue after a cavity wall is initially penetrated; and, therefore, the types of surgical procedures that can be performed with prior art safety trocars are thusly limited. Another disadvantage of prior art safety trocars is that the protective shields form an irregular surface or profile with the trocars resulting in increased resistance from tissue during penetration of a cavity wall, greater trauma and damage to tissue and possible jamming and trapping of tissue between the trocars and the safety shields.

SUMMARY OF THE INVENTION

Accordingly, it is a primary object of the present invention to overcome the above-mentioned disadvantages of prior art safety trocars.

Another object of the present invention is to optionally allow locking of a safety shield in an extended position from a solid, sharp distal end of a trocar of a safety trocar penetrating instrument.

The present invention has a further object in that a safety shield movable relative to a trocar within a portal sleeve is biased toward an extended position and can be selectively, releasably, locked in a retracted position exposing a solid, sharp, distal end of the trocar prior to or after penetration of a cavity wall.

Additionally, it is an object of the present invention to provide a safety trocar penetrating instrument having a safety shield movable between an extended position protecting a solid, sharp distal end of a trocar and a retracted position exposing the sharp distal end, the safety shield being distally biased toward the extended position and wherein the safety shield can be optionally automatically locked in the extended position when returned to the extended position by the distal bias.

Yet another object of the present invention is to construct a safety trocar penetrating instrument such that a distally biased safety shield can be manually pulled proximally toward a retracted position to expose a solid, sharp distal end of a trocar without requiring a force applied to the safety shield from tissue contact.

A further object of the present invention is use of a pin and slot mechanism to provide selective locking of a safety shield distally biased relative to a trocar, the pin extending externally of a housing to form a handle graspable by a surgeon to selectively move the safety shield between extended and retracted positions when the pin is moved along a longitudinal portion of the slot and to releasably lock the safety shield in the extended or retracted position when the pin is positioned in transverse portions of the slot.

A still further object of the present invention is to provide a safety trocar penetrating instrument having a trocar received in a safety shield movable relative to the trocar and disposed in a portal sleeve having an end secured in a housing, the safety shield and trocar extending through an opening in the housing and wherein adapter plugs can be positioned in the opening to form a seal with instruments of various sizes inserted therethrough when the safety shield and trocar are withdrawn from the portal sleeve.

Another object of the present invention is to provide a trocar, a safety shield receiving the trocar and movable relative to the trocar between extended and retracted positions and a portal sleeve mounting the safety shield wherein the trocar, the safety shield and the portal sleeve form a smooth profile in the retracted position to facilitate insertion in tissue forming a cavity wall.

An additional object of the present invention is to provide a safety trocar penetrating instrument having a trocar and a safety shield movable relative to the trocar between extended and retracted positions and wherein distal ends of the trocar and safety shield are configured in the retracted position to permit penetration of tissue of a cavity wall with a rotational motion providing relatively slower insertion with relatively greater control of the depth of insertion of the distal ends in tissue of the cavity wall.

Yet another object of the present invention is to control locking of a safety shield relative to a trocar in response to hand squeezing pressure of an end cap relative to the hub of a safety trocar penetrating instrument.

Some of the advantages of the present invention are that anatomical cavities of various sizes can be safety penetrated with a trocar to establish a portal in communication therewith, safety in handling and use of a safety trocar penetrating instrument is enhanced, penetration into additional tissue, such as into a cystic cavity or soft organ structure (e.g. ovarian cyst penetration or liver tissue biopsy), after penetration of a cavity wall can be accomplished with a single instrument, the types of surgical procedures utilizing a trocar can be expanded, safety trocar penetrating instruments can feasibly be employed in thoracic and cranial surgery, second puncture endoscopic or least invasive procedures are facilitated, exposure of medical personnel to inadvertent contact with the sharp tip of the trocar is minimized, a single puncture can be used for both insufflation and forming an endoscopic portal thereby simplifying procedures such as laparoscopy, trauma and damage to tissue is minimized, tissue jamming and trapping is avoided and safety trocar penetrating instruments according to the present invention can be inexpensively manufactured to be reusable or disposable.

The present invention is generally characterized in a safety trocar penetrating instrument including a trocar having a solid, sharp distal end or tip, a safety shield disposed concentrically around the trocar and movable relative to the trocar between an extended position protecting the sharp trocar tip and a retracted position exposing the sharp trocar tip, a hub receiving proximal ends of the trocar and safety shield and a portal sleeve receiving the safety shield to establish communication with an anatomical cavity upon penetration of the cavity by the trocar. The safety shield is distally biased toward the extended position, and a locking mechanism automatically locks the safety shield in the extended position after the safety shield is returned thereto by the distal bias after penetration of tissue forming the cavity wall or can optionally allow locking of the safety shield in the extended position with the safety shield being free to move toward the retracted position when the safety shield is not optionally locked in the extended position. The locking mechanism also provides selective, releasable, locking of the safety shield in the retracted position or can allow automatic locking of the safety shield in the retracted position. A housing securing a proximal end of the portal sleeve has an opening for passage of the safety shield and trocar therethrough and into the portal sleeve. The safety shield and trocar can be withdrawn from the portal sleeve, and adapter plugs can be positioned in the opening to form a seal with instruments of various sizes inserted therethrough. Various configurations for the distal ends of the trocar and the safety shield provide a smooth profile with the portal sleeve in the retracted position to facilitate penetration of tissue forming the cavity wall.

Other objects and advantages of the present invention will become apparent from the following description of the preferred embodiments taken in conjunction with the accompanying drawings.

BRIEF DESCRIPTION OF THE DRAWINGS

FIG. 1 is a broken side view, partly in section, of a safety trocar penetrating instrument according to the present invention.

FIG. 2 is a broken section of the hub and locking mechanism of the safety trocar penetrating instrument of FIG. 1.

FIG. 3 is a broken perspective view, partly in section, of an adapter plug for the safety trocar penetrating instrument of FIG. 1.

FIG. 4 is a broken view, partly in section, of the distal end of the safety trocar penetrating instrument of FIG. 1 with the safety shield in an extended position prior to penetrating tissue.

FIG. 5 is a broken view, partly in section, of the distal end of the safety trocar penetrating instrument of FIG. 1 with the safety shield in a retracted position during penetration of tissue.

FIG. 6 is a broken view, partly in section, of the distal end of the safety trocar penetrating instrument of FIG. 1 with the safety shield in an extended position after penetration of tissue.

FIG. 7 is a broken view, partly in section, of a modification of the distal end of a safety trocar penetrating instrument according to the present invention with the safety shield in the extended position.

FIG. 8 is a broken view, partly in section, of the distal end of the safety trocar penetrating instrument of FIG. 7 with the safety shield in the retracted position.

FIG. 9 is a broken view, partly in section, of a modification of a distal end of the safety trocar penetrating instrument according to the present invention with the safety shield in the extended position.

FIG. 10 is a broken view, partly in section, of the distal end of the safety trocar penetrating instrument of FIG. 9 with the safety shield in the retracted position.

FIG. 11 is a section taken along line 11—11 of FIG. 9.

FIG. 12 is a section taken along line 12—12 of FIG. 9.

FIG. 13 is a broken view, partly in section, of a modification of the distal end of a safety trocar penetrating instrument according to the present invention with the safety shield in the extended position.

FIG. 14 is a broken view, partly in section, of the distal end of a safety trocar penetrating instrument according to the present invention with the safety shield in the retracted position.

FIG. 15 is a broken view, partly in section, of a modification of the distal end of a safety trocar penetrating instrument according to the present invention with the safety shield in the extended position.

FIG. 16 is a broken view, partly in section, of the distal end of the safety trocar penetrating instrument of FIG. 15 with the safety shield in the retracted position.

FIG. 17 is a broken view, partly in section, of a modification of the distal end of a safety trocar penetrating instrument according to the present invention with the safety shield in the extended position.

FIG. 18 is a broken view, partly in section, of the distal end of the safety trocar penetrating instrument of FIG. 17 with the safety shield in the retracted position.

FIG. 19 is a broken view, partly in section, of a modification of the distal end of a safety trocar penetrating instrument according to the present invention with the safety shield in the extended position.

FIG. 20 is a broken view, partly in section, of the distal end of the safety trocar penetrating instrument of FIG. 19 with the safety shield in the retracted position.

FIG. 21 is a perspective view of a locking spring for the safety trocar penetrating instrument of the present invention.

FIG. 22 is a broken view, partly in section, of a modification of the hub and locking mechanism of the safety trocar penetrating instrument of the present invention.

FIGS. 23, 24, 25 and 26 are broken views, partly in section, illustrating stages of operation of the hub and locking mechanism of FIG. 22.

DESCRIPTION OF THE PREFERRED EMBODIMENTS

A safety trocar penetrating instrument 30 according to the present invention is illustrated in FIG. 1 and includes an elongate trocar 32, a safety shield 34 movably disposed concentrically around trocar 32, an elongate portal sleeve 36 concentrically disposed around safety shield 34, a hub 38 mounting trocar 32 and safety shield 34 and a housing 40 mounting portal sleeve 36. The hub 38 can be latched to housing 40 with the use of any suitable releasable mechanism, such as ball detents 42, allowing the hub to be removed from the housing withdrawing the trocar and safety shield from the portal sleeve. Accordingly, the safety trocar penetrating instrument 30 can be considered to be formed of a portal unit and a trocar unit, the portal unit including portal sleeve 36 and housing 40 and the trocar unit including trocar 32, safety shield 34 and hub 38.

Trocar 32 is preferably made of stainless steel with a cylindrical body having a diameter dependent upon the surgical procedure to be performed and the anatomical cavity to be penetrated. The trocar has a solid distal end 44 terminating at a sharp tip 46 for penetrating anatomical tissue. The distal end 44 can have various configurations; and, as shown in FIG. 1, the distal end 44 of the trocar has a pyramidal shape with three, equally spaced facets terminating proximally at a cylindrical neck 48 which, in turn, terminates proximally at a frusto-conical shoulder 50. A cylindrical body 52 extends proximally from shoulder 50 and terminates at a proximal end 54 secured to an end wall 56 of hub 38 by any suitable means, such as cement or threads. While the distal end of the trocar 32 is solid, the cylindrical body 52 can be either solid or tubular dependent upon manufacturing techniques utilized.

Hub 38 is preferably made of plastic to reduce cost and has an external configuration to cooperate with housing 40 to be easily grasped with one hand for use in penetrating tissue. Hub 38 is substantially rectangular in cross-section and includes, as best shown in FIGS. 1 and 2, four side walls extending from a front wall 58 to end wall 56 to provide a rearwardly flared outer profile with one side wall, indicated at 60, having a slot 62 therein.

Safety shield 34 is preferably made from a cylindrical length of a rigid or flexible material, such as stainless steel or plastic dependent upon use of the safety trocar penetrating instrument, and has a blunt distal end 64 with a configuration to extend beyond and protect sharp tip 46 of trocar 32 in an extended position. As best shown in FIG. 2, the safety shield 34 has a cylindrical tubular body 66 extending along the cylindrical body 52 of trocar 32 and through an opening 68 in front wall 58 of hub 38. Tubular body 66 terminates at a proximal end 70 disposed within the hub and carrying spaced annular ribs 72 and 74 between which is rotatably mounted an annular member or plate 76 having a pin 78 threadedly secured thereto and extending through slot 62, the pin 78 having a spherical end or knob to be easily grasped. A helical spring 80 is mounted in compression between plate 76 and end wall 56 of hub 38, and the spring 80 has longitudinally extending ends 82 received in apertures in plate 76 and end wall 56, respectively, such that the spring can be wound in torsion to bias the plate and the pin 78 carried thereby in a clockwise direction looking from the proximal end of the safety trocar penetrating instrument or upwardly looking at FIG. 1. The hub 38 can be formed in any suitable manner to facilitate winding of spring 80, such as molding the hub in parts or providing a rotatable insert for receiving a proximal, longitudinally extending end 82 of spring 80. The slot 62 formed in hub 38 has a longitudinal portion 84 aligned in parallel relation with a longitudinal axis of the trocar 32, a distal transverse portion 86 and a proximal transverse portion 88 having a recess 90 at the end thereof extending parallel with the longitudinal slot portion 84. If desired, for purposes to be explained hereinafter, the proximal transverse slot portion can extend in the same direction as the distal transverse slot portion as shown in dashed lines at 92.

Portal sleeve 36 is preferably made of a cylindrical length of stainless steel or other suitable, medically acceptable, plastic or metal material and can be rigid or flexible and transparent or opaque. The portal sleeve has a distal end 94 tapering to terminate at a peripheral edge 96 disposed in substantial alignment with a proximal edge of conical shoulder 50 such that the distal ends of the portal sleeve, the safety shield and the trocar present a substantially smooth profile to facilitate tissue penetration as shown in FIG. 5. The portal sleeve 36 has a threaded proximal end 98 removably received in an internally threaded nipple 100 extending from a front wall 102 of housing 40. Housing 40 is preferably made of plastic to reduce cost and has a rectangular configuration in cross-section corresponding to the cross-sectional configuration of hub 38 with a flared external profile adjacent front wall 102 to facilitate grasping during use. Recesses 104 and 106 are formed on opposite sides of nipple 100 and have a size and configuration to receive ball-type stopcocks 108 and 110, respectively, in a position such that the stopcocks are protected from inadvertent contact which could cause breakage or malfunction. A valve assembly 112 is mounted in housing 40 to control flow through the portal sleeve once the trocar unit is removed therefrom. The valve assembly can have any acceptable configuration and, as shown, includes a flange 114 having an annular configuration with a threaded periphery to be threadedly secured in housing 40, a plurality of spaced, spreadable legs 116 extending distally from flange 114 to produce a normally conical configuration tapering to an apex as illustrated in dashed lines in FIG. 1 and a conical, stretchable sleeve or membrane 118, preferably made of a rubber-like material such as silicone, having a configuration to tightly fit over legs 116 such that the sleeve and legs are normally biased to the closed position at the apex to prevent passage of fluids through the valve assembly. The legs 116 and flange 114 are preferably integrally made of unitary construction of a material, such as a plastic-like nylon, facilitating movement of medical instruments therethrough and allowing legs 116 to flex. The legs 116 are concentrically disposed around a central opening 120 in flange 114 and are slightly spaced from each other by gaps which terminate at curved relief recesses.

A cylindrical tube 122 is secured in the central opening 120 through flange 114, and a distal end of the cylindrical tube 122 engages a proximal annular portion of the valve assembly 112 at proximal ends of the legs 116. An adapter plug 124, as best shown in FIG. 3, is mounted on a proximal end of tube 122 and is integrally constructed of a flexible resilient material, such as Teflon, silicone rubber or plastic. The adapter plug 124 has a thick flange portion 126 with an annular recess 128 therein for receiving the proximal end of tube 122 and a cylindrical inner wall 130 extending from an inner edge of a central aperture 132 in the flange 126 to be snugly received within tube 122. The thickness of wall 130 is dependent upon the size of the instrument to be inserted through the portal sleeve 36 such that, if instruments smaller than the trocar unit are to be introduced into the body after the trocar unit is withdrawn from the portal sleeve, the adapter plug 124 is removed from the proximal end of tube 122 and another adapter plug is inserted therefor having an inner cylindrical wall of greater thickness to engage the smaller diameter instruments along the length of the inner cylindrical wall as shown in dashed lines at 134 in FIG. 3.

That is, the thickness of the inner wall 130 and the diameter of the tubular passage defined thereby will vary dependent upon the diameter of instruments passed through the portal unit, and the diameter of the tubular passage will be substantially the same as or slightly less than the outer diameter of an instrument passed therethrough to produce a seal therearound extending along the length of the inner wall. By utilizing various size adapter plugs with inner sealing walls to accommodate various size instruments, an effective seal can be produced for instruments varying greatly in size, for example from 2 mm to 12 mm.

In order to assemble the safety trocar penetrating instrument 30 as generally described above, the proximal end 70 of the safety shield 34, the spring 80 and the pin 78 are assembled within hub 38 with the spring 80 torsionally wound to bias plate 76 upwardly looking at FIG. 1 as previously described. It will be appreciated that plate 76 is rotatable in the annular groove between ribs 72 and 74 such that rotation of plate 76 does not cause rotation of the safety shield thereby assuring angular alignment of the distal ends of the trocar and the safety shield. The pin 78 will be, accordingly, biased distally along longitudinal slot portion 84 to a position adjacent distal transverse slot portion 86 and will be biased into distal transverse slot portion 86 due to the torsional bias from spring 80 to releasably lock the safety shield in the extended position. The trocar Unit formed by the trocar 32, the safety shield 34 and the hub 38 is then combined with the portal unit by passing trocar 32 and safety shield 34 through the central aperture 132 in adapter plug 124 and through housing 40 and portal sleeve 36 simultaneously spreading legs 116 of valve assembly 112 to produce a second seal along the safety trocar penetrating instrument. That is, the conical sleeve 118 acts as a seal to prevent passage of fluids thereby and tightly engages the trocar or other surgical instrument. With the hub 38 abutting the housing 40, a skirt 136 extending distally from the front wall 58 of hub 38 will be disposed within an open proximal end of the housing 40, and the detents 42 will hold the hub in position with respect to the housing. In this position, the distal end 94 of the portal sleeve will be disposed substantially in alignment with the proximal edge of conical shoulder 50 of the trocar to facilitate penetration by the trocar.

In use, it will be appreciated that with the pin 78 disposed in distal transverse slot portion 86, the safety shield 34 cannot move proximally within portal sleeve 36 thereby assuring that the sharp tip 46 of the trocar is protected to prevent inadvertent contact during handling and use. When it is desired to penetrate an anatomical cavity, the blunt distal end 64 of the safety shield is positioned in abutment with the tissue T to be penetrated as illustrated in FIG. 4, and a finger is utilized to manually move pin 78 counter-clockwise against the torsional bias of spring 80 to be aligned with the longitudinal portion 84 of slot 62. With the pin 78 in this position, when the distal end 64 of the safety shield is forced against the tissue to be penetrated, the safety shield 34 will move proximally against the bias of spring 80 to a retracted position as illustrated in FIG. 5. With the safety shield in the retracted position, penetration through the tissue with minimal tissue jamming and trapping is accomplished due to the smooth profile of the distal end of the safety trocar penetrating instrument. Pin 78 will not enter proximal transverse slot portion 88 when the pin is aligned therewith due to the torsional or rotational bias of spring 80 in the opposite direction; and, thus, once the anatomical wall has been completely penetrated such that the force of tissue against the distal end of the safety probe is removed, spring 80 will bias the safety shield distally such that the safety shield returns to the extended position as illustrated in FIG. 5 to protect the sharp tip 46 such that the sharp tip is exposed only during the tissue penetrating step. Once the safety shield has returned to the extended position, the pin 78 automatically enters distal transverse slot portion 86 due to the rotational bias of spring 80 to lock the safety shield in the extended position. If automatic locking of the safety shield 34 is not desired, the spring 80 is not wound during assembly such that pin 78 is not rotationally biased. Accordingly, after spring 80 returns the safety shield 34 to the extended position when the force on the safety shield distal end from tissue resistance is removed, the pin will not enter distal transverse slot portion and the safety shield will not be locked in the extended position. Thus, the surgeon has the option of locking the safety shield in the extended position by manually moving the pin 78 into distal transverse slot portion 86 or allowing the safety shield to be free to move proximally by not moving pin 78 into distal transverse slot portion 86.

If, after penetration into the anatomical cavity, it is desired to penetrate additional tissue, the surgeon can selectively release the safety shield from the extended position by moving pin 78 counter-clockwise to be aligned with longitudinal slot portion 84. If the protection provided by the safety shield is not required or desired for further procedures, the pin 78 can be moved into recess 90 of proximal transverse slot portion 88 to releasably lock the safety shield in the retracted position or a position further withdrawn into portal sleeve 36 dependent upon the longitudinal position of proximal transverse slot portion 88. Where proximal transverse slot portion 92 extending in the same direction as the distal transverse slot portion, is provided, the safety shield will automatically lock in the retracted position when pin 78 is aligned with proximal transverse slot portion 92 due to the rotational bias from spring 80. If slot portion 92 is positioned proximally of pin 78 when the safety shield is in the retracted position, the safety shield will not automatically lock during use but, rather, the pin will have to be manually pulled back to alignment with slot portion 92 to lock the safety shield in the retracted position.

While plate 76 rotates within Hub 38, safety shield 34 does not rotate therewith to maintain alignment with trocar 32. Various index configurations to maintain rotational alignment between the safety shield and the trocar can be used, if desired; and, for example, the safety shield can be splined with the trocar.

Once the trocar has been used to penetrate tissue to the extent desired by the surgeon, the portal sleeve 36 can be left in place by withdrawing the trocar unit from the portal unit; and, once the trocar unit is withdrawn, valve assembly 112 will prevent fluid flow through the portal sleeve 36 and housing 40. If it is desired to then insert an instrument having a diameter less than the diameter of trocar 32, adapter plug 124 is removed from the proximal end of tube 122 and replaced with an adapter plug having a central aperture and tubular passage formed by the inner wall 130 of a diameter corresponding to, or less than, the smaller instrument to be inserted.

For procedures where it is desired to gain access to an area of an anatomical cavity substantially offset from the longitudinal axis of the safety trocar penetrating instrument, the portal sleeve can have a normal, non-linear configuration such that, once penetration is completed and the trocar unit is withdrawn from the portal unit, the portal sleeve will return to the non-linear configuration. For example, the portal sleeve is shown in dashed lines in FIG. 6 as having a curved configuration 138 to which the portal sleeve returns when the trocar and safety shield are withdrawn. Where the portal sleeve, the trocar and the safety shield are made from a flexible material, the safety trocar penetrating instrument can be employed in flexible endoscopy wherein, for example, the safety trocar penetrating instrument can be inserted in an operating channel of a flexible endoscope. Additionally, by forming the portal sleeve, the trocar and the safety shield from a flexible material, the safety trocar penetrating instrument can be inserted through non-linear anatomical passages.

In accordance with the present invention, the distal ends of the safety shield and the trocar are specifically configured to cooperate to form a smooth profile minimizing resistance during tissue penetration. In the embodiment illustrated in FIGS. 1 and 4–6, the distal end 44 of the trocar 32 has three, generally triangular, flat sides or facets 140 tapering distally to sharp, tissue penetrating tip 46 from cylindrical neck 48. The junctions 142 of the flat sides 140 with the cylindrical neck 48 are curved to have a scalloped configuration, and the frusto-conical shoulder 50 tapers distally from a circular junction 144 with cylindrical trocar body 52 to a smaller circular Junction 146 with neck 48. The distal end 64 of the safety shield 34 is configured to mate with the distal end of the trocar when the safety shield is in the retracted position as best shown in FIG. 5. More particularly, the safety shield distal end has a tapering conical wall 148 having an inner surface 149 disposed at the same angle relative to the longitudinal axis of the trocar as the angle of the outer surface of shoulder 50 relative to the trocar longitudinal axis. Conical wall 148 joins cylindrical safety shield body 150 proximally and distally terminates at a cylindrical inner surface 152 having an axial length substantially equal to the axial length of trocar neck 48. The peripheral distal edge 154 of the safety shield is shown as being-circular, which is preferred if the trocar tip is conical rather than faceted; however, distal edge 154 can be scalloped or formed of curved segments 156, as shown in dashed lines in FIG. 4, corresponding in radius and arc of curvature to curved junctions 142 to provide exact mating of the safety shield and the trocar in the retracted position. As shown in FIG. 5, when the safety shield is in the retracted position, conical wall 148 is in contact with shoulder 50 along the length thereof while inner surface 152 is in contact with neck 48. Accordingly, the distal end of the safety trocar penetrating instrument has a smooth profile presenting minimal resistance to tissue as a cavity wall is penetrated. More particularly, the angle of the outer surface of conical wall 148 is the same as the angle of the trocar tip relative to the trocar longitudinal axis such that wall 148 forms a smooth continuation of the trocar tip leading to the distal end of portal sleeve 36. During penetration, the peripheral distal edge 154 of the safety shield 34 initially engages the tissue and then moves proximally as penetration continues until the safety shield is in the retracted position shown in FIG. 5, it being noted that the mating configurations of the safety shield and trocar distal ends produces a positive stop to limit proximal movement of the safety shield.

A modification of the safety shield distal end 64 is illustrated in FIGS. 7 and 8 at 158 with the primary difference being that, while the inner surface 159 of "conical" wall 148 has a configuration mating with neck 48 and shoulder 50 of the trocar tip, the outer surface of wall 148 has flat sides or facets 160 having configurations to form extensions of trocar tip facets 140 when the safety shield is in the retracted position shown in FIG. 8. To this end, the number of safety shield facets 160 equals the number of trocar facets 140 and the angular or rotational orientation of the safety shield relative to the trocar is such that junction lines or edges 162 between the trocar facets 140 are aligned with junction lines or edges 164 between the safety shield facets 160. The proximal end of each trocar facet 140 has a width substantially equal to the width of the distal end of each safety shield facet 160 aligned therewith, and the safety shield facets 160 continue at the same angle to the trocar longitudinal axis as the trocar facets 140 to terminate adjacent the distal peripheral edge 96 of portal sleeve 36. The distal end of each safety shield facet 160 can be scalloped or formed of curved segments to conform in radius and arc of curvature to the junctions 142 at a proximal end of each aligned trocar facet 140 to reduce gaps therebetween and further minimize tissue resistance during penetration. The trocar tip can have any number of facets arranged at regular or irregular positions; and, in accordance with the modification of the present invention of FIGS. 7 and 8, the safety shield will have a number of facets equal to and similarly arranged with the trocar facets to produce a continuous smooth profile during penetration.

Another modification of the distal end of the safety trocar penetrating instrument according to the present invention is illustrated in FIGS. 9–12 wherein the trocar tip has a plurality of flat facets 166 as described above; however, a depression in the form of a hole or recess 168 is formed in a proximal portion of each facet, as shown in FIGS. 9 and 11, and the facets 166 extend proximally to terminate adjacent the distal peripheral edge 96 of the portal sleeve 36. The safety shield 34 has a distal end 64 formed of a plurality of fingers 170 equal to the number of trocar facets 166, and each finger 170 is aligned with a trocar facet 166. The distal ends 172 of fingers 170 are rounded, and each finger 170 carries a smoothly curved, inwardly protruding nub 174, as shown in FIG. 12, having a configuration to be received in depressions 168. Accordingly, when the safety shield is moved to the retracted position during penetration of tissue as shown in FIG. 10, nubs 174 will be received in depressions 168 such that the fingers 170 form extensions of the trocar tip facets 166 providing a smooth profile presenting minimal resistance to tissue when a cavity wall is penetrated, and the hubs 174 received in the depressions 168 serve as a positive stop to limit proximal movement of the safety shield.

Another modification of the distal end of the safety trocar penetrating instrument according to the present invention is illustrated in FIGS. 13 and 14 wherein the trocar tip has a plurality of flat facets 166 as described above extending proximally to terminate adjacent the peripheral distal edge 96 of the portal sleeve 36. The safety shield 34 has a distal end 64 formed of a resilient, flexible material, preferably a rubber-like material such as silicone or latex, having a configuration to fit closely over the trocar tip. The safety shield distal end 64 defines a plurality of legs 176 equal to the number of trocar facets 166 with each leg 176 being aligned with a trocar facet 166. The legs 176 have lateral edges 177 joined at radiused ends 178 aligned with the distal peripheral edge 96 of the portal sleeve 36, as shown in FIG. 13, and tapering distally along the trocar facets 166 from the radiused ends 178 to an apex. 180 forming a closed, blunt end disposed distally from the sharp trocar tip 46. In the extended position for the safety shield, the lateral edges 177 extend along the longitudinal axis of the trocar; and, when the safety shield is moved to the retracted position during penetration of tissue as shown in FIG. 14, the legs 176 will flex or spread outwardly from the longitudinal axis of the trocar and form a smooth profile with the trocar facilitating insertion in tissue of a cavity wall. By forming the safety shield distal end of a resilient material, the material itself can provide a bias for returning the safety shield to the extended position upon removal of force from tissue contact such that the structural arrangement at the proximal end of the safety trocar penetrating instrument can be simplified. By selecting the material forming the safety shield distal end to provide a limited degree of outward expansion for the legs, a positive stop can be obtained limiting proximal movement of the safety shield.

Another modification of the distal end of the safety trocar penetrating instrument according to the present invention is shown in FIGS. 15 and 16 wherein the trocar tip tapers from the neck 48 to the sharp trocar tip 46 to define a conical distal end, and a helical thread 180 extends along the conical trocar tip from the neck to the sharp tip. The safety shield distal end 64 includes tapering conical wall 148 having an inner surface disposed at the same angle relative to the longitudinal axis of the trocar 32 as the angle of the outer surface of shoulder 50 relative to the trocar longitudinal axis. Conical wall 148 joins cylindrical safety shield body 150 proximally and distally terminates at cylindrical inner surface 152 having an axial length substantially equal to the axial length of trocar neck 48. A helical thread 182 extends along the tapering conical wall 148 from cylindrical safety shield body 150 to a circular, peripheral distal edge 154 of the safety shield. Threads 180 and 182 are like handed extending in the same angular direction with the longitudinal axis of the trocar, and a proximal end of the thread 180 merges with a distal end of the thread 182 when the safety shield is in the retracted position shown in FIG. 16 with conical wall 148 in contact with shoulder 50 along the length thereof while inner surface 152 is in contact with neck 48. Accordingly, the distal end of the safety trocar penetrating instrument forms a smooth profile as well as a continuous thread extending along the trocar tip and the conical wall 148 of the safety shield facilitating insertion of the distal end of the safety trocar penetrating instrument in tissue forming a cavity wall. With the embodiment of FIGS. 15 and 16, the distal end of the safety trocar penetrating instrument is inserted in tissue with a rotational motion providing relatively slower penetration with greater control of penetration depth and is particularly advantageous for thoracic and brain surgery.

The modification of FIGS. 16 and 17 can also be utilized for particular procedures with no threads such that the conical tip cooperates with the conical wall of the safety shield to produce a smooth, continuous conical configuration during penetration. That is, when inner surface 152 is moved proximally to contact neck 48, conical wall 148 will be an extension of the conical trocar tip.

Another modification of the distal end of the safety trocar penetrating instrument is illustrated in FIGS. 17 and 18 wherein the trocar tip is the same as that described for FIGS. 13 and 14, and the safety shield distal end 64 is formed of a resilient, flexible, compressible and expandable material that can fold or wrinkle, the material defining a curved wall 184 having a predetermined configuration in the extended position shown in FIG. 17. The curved wall 184 gradually tapers distally toward the blunt, peripheral distal edge 154 of the safety shield 34 disposed distally from the sharp tip 46 of the trocar 32. During penetration of tissue of the cavity wall, safety shield 34 will be compressed proximally in the retracted position, as shown in FIG. 18, exposing the sharp trocar tip 46. By forming the curved wall 184 of minimal thickness, a smooth profile is maintained with the trocar facets 166 in the retracted position to minimize tissue resistance. By forming the safety shield distal end of a resilient material, the material itself can provide a bias for returning the safety shield to the extended position upon removal of force from tissue contact, and the amount of material compressed in the retracted position can act as a positive stop limiting proximal movement of the safety shield.

Another modification of the distal end of the safety trocar penetrating instrument is illustrated in FIGS. 19 and 20 wherein the trocar tip is the same as that shown in FIGS. 7 and 8, and the safety shield distal end 64 is formed of a resilient, flexible, compressible and expandable material configured to fit closely over the trocar tip and capable of folding or collapsing along fold lines 186 disposed concentrically with the trocar tip. In the retracted position shown in FIG. 20, the safety shield 34 is folded or collapsed along the fold lines 186 forming an accordion-like configuration with annular ribs 188. The amount of material compressed or folded in the retracted position can be selected such that the distal edge 154 of the safety shield is disposed adjacent junction 142 in the retracted position with the ribs 188 defining gradually increasing diameters from the distal edge 154 to merge with the distal peripheral edge 96 of the portal sleeve along the same angle as the trocar facets 140 with the trocar longitudinal axis to form a smooth profile facilitating penetration in tissue of a cavity wall. By forming the safety shield distal end of a resilient material, the material itself can provide a bias for returning the safety shield to the extended position upon removal of force from tissue contact, and the amount of material compressed in the retracted position can act as a positive stop limiting proximal movement of the safety shield.

A modification of a locking mechanism for the safety trocar penetrating instrument of the present invention is shown in FIG. 22 wherein the trocar unit including trocar 32, safety shield 34 and hub 38 is illustrated. The hub 38 is adapted to be coupled with housing 40 as described in connection with FIG. 1 and includes front wall 58 having opening 68 therein receiving the tubular body 66 of the safety shield 34. Tubular body 66 terminates at proximal end 70 disposed within the hub and carrying an annular flange 190 which can be secured on proximal end 70 or formed as an integral part thereof. A slot 192 is formed in tubular body 66 and extends longitudinally from flange 190 in a distal direction in parallel alignment with the trocar longitudinal axis. Cylindrical body 52 of trocar 32 has an opening 196 formed therein adjacent a proximal face of flange 190. Cylindrical body 52 terminates at proximal end 54, and a lumen 197 is formed in cylindrical body 52. Proximal end 54 is secured in a central opening in an annular member 198 releasably received, for example via a threaded connection, in an open proximal end 200 of hub 38. While the trocar body 52 and member 198 are shown as being made as one piece, the body 52 and member 198 can be made as separate parts secured together in any desirable manner, such as by welding, cement or threads for example. A positioning rod 199 has ends secured, respectively, to front wall 58 and member 198, the rod 199 passing through an aperture in flange 190. A helical spring 202 is disposed over rod 199 and is mounted in compression between member 198 and flange 190 to bias the safety shield to the extended position with the rod 199 preventing relative rotational movement of the safety shield and trocar. Alternatively, spring 202 and rod 199 may be replaced with a telescoping-type spring having ends secured, respectively, to wall 58 and member 198, or any other spring suitable for biasing the safety shield to the extended position. An end cap 206 has a lip 208 extending around the periphery of member 198 such that the end cap can move longitudinally, axially relative to hub 38. A hollow stem 210 extends centrally from end cap 206 to be slidably received in proximal end 54 of trocar 32, and a helical spring surrounds stem 210 and is mounted in compression between end cap 206 and member 198 to bias the end cap proximally relative to the hub. A locking spring 212 illustrated in FIG. 21 has a curved end 214 secured within trocar 32 and joined to a body 216 bifurcated to form a proximally extending deactuating arm 218 and a substantially transversely extending abutment arm 220, the abutment arm passing through opening 196 in trocar 32 and having a curved head 222 terminating at a distally extending finger 224. A deactuator or release arm 226 is mounted in stem 210 and has a protrusion 228 positioned to engage arm 220 of the locking spring.

In operation, the locking mechanism is normally in the condition shown in FIG. 22 with abutment arm 220 passing through opening 196 and finger 224 disposed above cylindrical body 52 at a position to engage the proximal face of flange 190 such that the safety shield 34 cannot move proximally and is, therefore, locked in the extended position protecting the sharp tip of the trocar 32. When tissue of an anatomical cavity wall is to be penetrated, the hub 38 and the housing 40 are gripped in one hand with the palm of the hand engaging end cap 206; and, when the hand is squeezed, end cap 206 is moved distally along hub 38 against the bias of spring 211 causing the protrusion 228 of deactuator 226 to move deactuating arm 218 distally buckling the locking spring 212 and causing the abutment arm 220 to move within the opening 196 in cylindrical body 52 and out of the path of movement of flange 190 as shown in FIG. 23. Accordingly, the safety shield is now in an unlocked state and able to move proximally from the extended position.

When the safety trocar penetrating instrument is forced into the tissue, the safety shield will move proximally against the force of spring 202 and slide over the curved head 222 of the abutment arm of the locking spring causing the locking spring to move further into the opening 196 thereby freeing deactuating arm 218 from the protrusion 228 on the deactuator 226 as shown in FIG. 24. Once the safety shield has moved to the retracted position, the flange 190 will have passed proximally beyond the opening 196 and out of engagement with abutment arm 220, and the slot 192 will be vertically sligned with the opening 196 thereby allowing the abutment arm 220 to return to its normal position with deactuating arm 218 overlapping protrusion 228 is shown in FIG. 25. When an anatomical cavity has been penetrated such that the force of tissue against the distal end of the safety shield is removed, the safety shield will return to the extended position under the biasing force from spring 202, camming over the curved head 222 of abutment arm 220 with the abutment arm then returning to the locking position as shown in FIG. 26. At this time, the end cap 206 remains in the compressed state from gripping by the hand such that the deactuator 226 cannot release the locking spring, and the safety shield automatically locks in the extended position. If it is desired to release the safety shield for further use of the trocar, the end cap must be released to return to the position illustrated in FIG. 22 whereupon squeezing the end cap again will release the safety shield for further penetration of tissue if desired.

Inasmuch as the present invention is subject to many variations, modifications and changes in detail, it is intended that the subject matter discussed above and shown in the accompanying drawings be interpreted as illustrative and not in a limiting sense.

What is claimed is:

1. A safety trocar penetrating instrument comprising an elongate, tubular portal sleeve having a distal end and a proximal end;

a housing coupled with said proximal end of said portal sleeve and having a valve therein for controlling fluid flow through said housing and said portal sleeve and for allowing passage of instruments therethrough;

a trocar disposed within said portal sleeve and having a longitudinal axis, a proximal end and a solid, distal end terminating at a sharp tip beyond said distal end of said portal sleeve for penetrating tissue;

a safety shield disposed between said portal sleeve and said trocar and having a proximal end and a distal end and being movable between an extended position with said safety shield distal end protruding distally of said trocar tip and a retracted position with said safety shield distal end disposed proximally of said trocar tip to expose said trocar tip;

a hub abutting said housing for receiving said proximal ends of said trocar and said safety shield, said trocar and said safety shield passing through said a valve in said housing;

bias means for biasing said safety shield toward said extended position and for permitting said safety shield to move proximally to said retracted position in response to a proximally directed force applied to said safety shield distal end, said bias means returning said safety shield to said extended position when the force applied to said safety shield distal end is removed; and stop means for limiting proximal movement of said safety shield wherein said trocar distal end includes a plurality of angled, flat sides joined at edges and said safety shield distal end includes a plurality of legs equal to said plurality of sides and having lateral edges aligned with said edges of said sides and wherein said legs taper distally along said sides to an apex disposed distally of said tip in said extended position, said legs being formed of a resilient, flexible material allowing said legs to expand outwardly from the trocar longitudinal axis in said retracted position.

2. A safety trocar penetrating instrument as recited in claim 1 wherein said stop means includes a portion of said legs configured to limit outward expansion of said legs in said retracted position.

3. A safety trocar penetrating instrument as recited in claim 2 wherein said bias means is formed by a portion of said legs.

* * * * *